(12) United States Patent
Trasciatti et al.

(10) Patent No.: US 7,678,571 B2
(45) Date of Patent: Mar. 16, 2010

(54) PROCEDURE FOR THE LARGE-SCALE T-LYMPHOCYTES CULTURE IN A HOMOGENEOUS SYSTEM

(75) Inventors: Silvia Trasciatti, San Giuliano Terme (IT); Maria Luisa Nolli, Milan (IT); Luigi Cavenaghi, Milan (IT); Nadia De Bernardi, Inveruno (IT)

(73) Assignee: Abiogen Pharma S.p.A., Pisa (IT)

( * ) Notice: Subject to any disclaimer, the term of this patent is extended or adjusted under 35 U.S.C. 154(b) by 334 days.

(21) Appl. No.: 10/530,108

(22) PCT Filed: Oct. 6, 2003

(86) PCT No.: PCT/EP03/11024

§ 371 (c)(1),
(2), (4) Date: Apr. 1, 2005

(87) PCT Pub. No.: WO2004/031370

PCT Pub. Date: Apr. 15, 2004

(65) Prior Publication Data

US 2006/0034802 A1  Feb. 16, 2006

(30) Foreign Application Priority Data

Oct. 4, 2002 (IT) .......................... MI2002A2118

(51) Int. Cl.
*C12N 5/071* (2010.01)
*C12N 5/00* (2006.01)
*C12N 5/02* (2006.01)

(52) U.S. Cl. ..................................... 435/372.3; 435/386

(58) Field of Classification Search ........................ None
See application file for complete search history.

(56) References Cited

U.S. PATENT DOCUMENTS 6,491,678 B1 * 12/2002 Rubinstein et al. .......... 604/410

FOREIGN PATENT DOCUMENTS

WO   WO 94/26284   * 11/1994

OTHER PUBLICATIONS

Visonneau et al., 2000, Clin. Cancer. Res. vol. 6: 1744-1754.*
Woolley et al., 2000, Arth. Res. vol. 2: 65-74.*
Gambacorti-Passerini et al., 1988, Tumori, vol. 74: 523-530.*
Nunclon Cell factory FAQ, 2008, pp. 1-2.*
Schumpp et al., 1990, J. Cell Sci. vol. 97: 639-647.*
Carswell et al., 2000, Biotech and Bioeng. vol. 3: 328-338.*
O'Connor, R. et al. (1991) "Growth factor requirements of childhood acute t-lymphoblastic leukemia: correlation between presence of chromosomal abnormalities and ability to grow permanently in vitro" Blood 77:1634-1645.
Cesano, A. et al. (1992) "Two unique human leukemic t-cell lines endowed with a stable cytotoxic function and a different spectrum of target reactivity analysis and modulation of their lytic mechanisms" In Vitro Cell. Dev. Biol. 18A:648-656.
Cesano, A. et al. (1996) "Use of a lethally irradiated major histocompatibility complex nonrestricted cytotoxic t-cell line for effective purging of marrows containing lysis-sensitive or -resistant leukemic targets" Blood 87:393-403.
Cesano, A. et al. (1996) "Antitumor efficacy of a human major histocompatibility complex nonrestricted cytotoxic t-cell line (tall-104) in immunocompetent mice bearing syngeneic leukemia" Cancer Research 56:444-4452.
Berger et al. (2002) "Large-scale generation of mature monocyte-derived dendritic cells for clinical application in cell factories" Journal of Immunological Methods 268:131-140.
Cesano et al. (1996) "Phase I clinical trial with a human major histocompatibility complex nonrestricted cytotoxic t-cell line (TALL-104) in dogs with advanced tumors" Cancer Research 56:3021-3029.
Tuyaets et al. (2002) "Generation of large numbers of dendritic cells in a closed system using cell factories" Journal of Immunological Methods 264:135-151.
Visonneau et al. (1997) "Successful treatment of canine malignant histicytisis with the human major histocompatibility complex non-restricted cytotoxic t-cell line TALL-104" Clinical Cancer Research 3:1789-1797.
Pierson, B.A. et al. 1996 "Production of Human Natural Killer Cells for Adoptive Immunotherapy Using a Computer-Controlled Stirred-Tank Bioreactor" *J Hematology* 5:475-483.

* cited by examiner

*Primary Examiner*—Amy E Juedes
(74) *Attorney, Agent, or Firm*—Knobbe Martens Olson & Bear LLP

(57) ABSTRACT

The present invention refers to a procedure for the large-scale amplification of human lymphocytic cell lines for therapeutic use, consisting of a homogeneous culture system. The claimed invention also refers to the production of therapeutic doses of lymphocytic cells cultured homogeneously.

12 Claims, 1 Drawing Sheet

Number of cells /ml (-♦-), glucose levels (full bar).

PROCEDURE FOR THE LARGE-SCALE T-LYMPHOCYTES CULTURE IN A HOMOGENEOUS SYSTEM

RELATED APPLICATIONS

This application is a U.S. National Phase under 35 U.S.C. 371 of International patent application No.: PCT/EP2003/011024, filed Oct. 6, 2003 designating the United States of America and published in English on Apr. 15, 2004 as WO 2004/031370, which claims the benefit of priority of Italian Patent Application No.: MI2002A 002118, filed Oct. 4, 2002.

FIELD OF THE INVENTION

The field of the invention concerns the in vitro cell culture and the large-scale expansion of isolated human cells.

PRIOR ART

An approach to the anti-tumour therapy is based on the use of ex vivo isolated cell lines or cells endowed with cytotoxic activity.

In the early '90, a number of T-lymphocyte cell lines derived from children with acute T-cell lymphoblastic leukemia, named TALL, were isolated. They include T-cell lines TALL-104, TALL-107, TALL-103/2, described by O'Connor et al. (Blood, 1991, 77: 1534-1545) and by Cesano and Santoli (In Vitro Cell. Dev. Biol., 1992, 28: 648-656). They exhibit such interesting characteristics that they are now-successfully used in the treatment of tumours in animal models and in man (Cesano et al., Blood 1991, 87:393-403; Cesano et al., Cancer Res., 1996, 56: 3021-3029, U.S. Pat. No. 5,272,082; U.S. Pat. No. 5,683,690; U.S. Pat. No. 5,702,702).

TALL cell lines are endowed with cytotoxic, specifically anti-tumour, activity and are active against different types of tumours: the main characteristic of these cells is that they are MHC non-restricted (Cesano et al., J. Immunol., 1993, 151: 2943-2957) and, therefore, can be administered to any patient, independently of the histocompatibility antigens phenotype. Furthermore, unlike some types of cytotoxic lymphocytes, such as for example TIL and LAK, TALL cell lines do not need, after in vivo administration, a concomitant treatment with lymphokines. This is a further advantage of said cells, since the simultaneous administration of lymphokines has several drawbacks.

Moreover, TALL lymphocytes have been successfully tested in a variety of tumours. These are the reasons why they are considered an interesting therapeutic alternative. However, the cell expansion systems used so far are limiting because the cells prepared for adoptive immunotherapy derive from cultures grown in single flasks, as described in Cesano et al., Cancer Res., 1996 56: 4444-4452 and Visonneau et al., Clin. Cancer Res., 1997, 3: 1789-1797, although large-scale cell cultures apparatuses like those used in the preparation of monoclonal antibodies and recombinant proteins have long been utilised. Therefore, a large-scale culture system suitable for cells of this type is highly desirable.

SUMMARY

It is an object of the present invention to provide a process for the TALL lymphocytes large-scale expansion and growth based on the use of a homogeneous culture system. The expression "large-scale amount of TALL lymphocytes" refers to $1 \times 10^9$ cells at least.

In particular, the fermentor or homogeneous system used in the claimed process is a cell-factory, preferably consisting of a stack of 10 chambers. The lymphocytes that may be expanded according to the present procedure are selected from the group consisting of TALL-104, TALL-107, TALL-103/2, optionally genetically modified.

According to a further embodiment the invention concerns a process of cell—sampling said process based on the sealing of the filling collet of the bag which creates at least a sampling chamber containing a number of cells sufficient for sampling.

Figure 1:
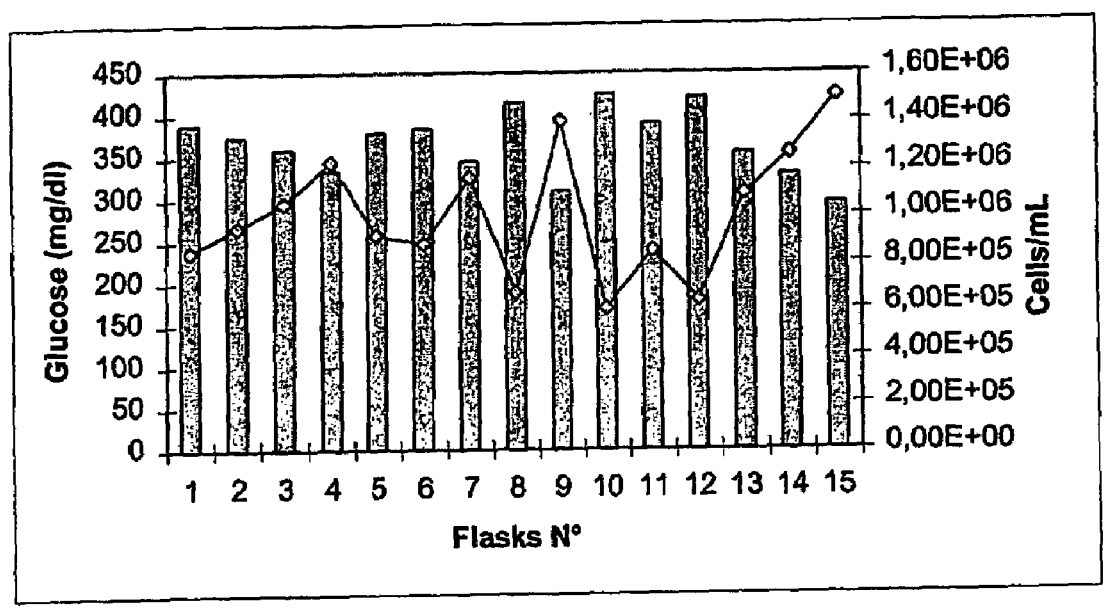
FIG. 1 is a chart illustrating the glucose levels and the cellular density of TALL cells grown in flask.

The following parameters were determined in 15 flasks of TALL: cells number/ml (-♦-) and glucose levels (full bar).

DETAILED DESCRIPTION OF THE INVENTION

The invention refers to a procedure for the large-scale expansion of TALL lymphocytes, wherein at least $1 \times 10^9$ cells are cultured in a homogeneous system preferably consisting of a single fermentation unit.

TALL (T-cell acute lymphoblastic leukemia) lymphocytes are cytotoxic T-lymphocyte lines derived from a pediatric patient with lymphoblastoid leukemia and include TALL-104, TALL-107, TALL-103/2 lines, as described in O'Connor et al., Blood, 1991, 77, 1534:1545, and Cesano and Santoli, In Vitro Cell. Dev. Biol., 1992, 28: 648-656). The preferred cell line is TALL-104. TALL cells may also be modified genetically.

They have so far been exclusively amplified in single flasks up to an obtainable maximum of approx. $1 \times 10^8$ cells/T175 flask.

Therefore, the preparation of bags containing therapeutically effective quantities of cells comprised in the range from $10^5$ to $10^{12}$ cells, preferably from $1 \times 10^7$ to $1 \times 10^{10}$ and still more preferably from $1 \times 10^8$ to $2.5 \times 10^9$ involved, until now, the simultaneous amplification of a large number of single flasks.

According to the definitions of the invention the growth in single flasks represents a heterogeneous culture system since each flask represents a different culture microenvironment. Consequently, and in accordance with FDA's guidelines: "Guidance for Industry: Guidance for human somatic cell therapy and gene therapy" (CBER, March 1998, Point III) of the US Department of Health—which recommends a separate control of each mixture of cells prepared in an independent system—the cells derived from each single flask according to the prior art methods represent different lots and, therefore, are to be controlled independently. It follows that the development of a homogeneous culture system of cells for therapeutic use, and especially of TALL cells, represents an enormous advantage also as far as lot controls are concerned.

Furthermore, the amplification in a heterogeneous system, which consists of a number of single flasks, may bring about high risks of contamination due to the repeated handling operations to be performed by the operator.

TALL cells usually grow in suspension but, surprisingly, they cannot be amplified or expanded in known systems for the industrial scale-up of cells of this type, e.g. spinner flask or miniPERM. Therefore, when the amount of cells to be produced exceeds $10^9$, such as for example for the production of therapeutic doses of $2.5 \times 10^9$ cells at least, the steps of cell—expansion become extremely complex since the largest flasks (T175) commercially available allow the obtainment of 1.5-2×10⁸ TALL cells at maximum.

The applicant has surprisingly found that said cells can be efficiently grown and expanded in a homogeneous system such as a cell-factory which is normally used for anchorage-dependent cells. Conversely, the spinner flask or other fermentors conventionally used for the large-scale growth of cells in suspension, e.g. hybridoma cells exhibiting growth characteristics similar to TALL cells, result to be inappropriate.

The expression "large-scale production" means the production of at least $1 \times 10^9$ TALL cells in a homogeneous system.

In the procedure of the invention, the data referred to the number of cells have a tolerance of approx. 5%, which represents the possible error in the cell count determined in Burker's chamber. For example, the indication of $1 \times 10^6$ cells actually refers to a number of cells of $0.95 \times 10^6$ to $1.05 \times 10^6$. The error of measurement is variable and depends on the method of measurement adopted.

According to the procedure of the invention, the TALL expansion in a cell-factory is preferably preceded by a pre-expansion consisting in a series of volumetric expansions in the same flask (wherein for flask is intended a cell culture container) by means of successive additions of fresh complete medium to the culture and by transfer passages of the whole culture into higher-volume flasks and finally into the highest-volume and largest-surface flasks commercially available such as the T175 flasks.

According to a preferred feature of the present invention, the pre-expansion is performed until obtaining about $3\text{-}4 \times 10^8$ total cells of which about $2\text{-}2.5 \times 10^8$ cells are used for the inoculation into each cell-factory and about $1\text{-}1.5 \times 10^8$ cells are in parallel maintained In T175 culture flasks.

Splitting of the cell culture, performed to bring back the cellular density values to the optimal inoculum values, i.e. 0.7 to $1 \times 10^8$ cells/ml, is referred to herein as "passage". At this density the cells rapidly reach a density of approx. $2.5 \times 10^9$ cells/ml.

Pre-amplification is preferably carried out in a complete medium, more preferably IMDM, containing 2 mM glutamine, foetal bovine serum (FBS) in concentration from 2 to 20%, preferably 5%, and cytokines, preferably interleukins, and more preferably IL-2 or IL-15. IL-2 is preferably added in an amount of 100 IU/ml every 48-72 hrs. In the homogeneous system, the medium of the amplification phase is the same as that of the pre-amplification phase, but foetal bovine serum is replaced, at least partially, by human serum AB. Said replacement can also be performed before cell—transfer to the homogeneous cell culture system, for example in the last passages of the pre-amplification phase. IMDM may be replaced by other culture media, such as for example RPMI, Ham's-F12, etc. The medium is preferably antibiotic-free.

A medium preferably IMDM containing 2 mM glutamine but antibiotic-free is referred to herein as "complete medium"; it may be supplemented with FBS or human serum.

Interleukins, preferably IL-2 or IL-15, are added to the cell culture medium every 48 to 72 hrs, in a final concentration of 50 to 150 IU/ml, more preferably of 100 IU/ml.

The cells are incubated at 37° C. and in an air mixture comprising preferably from 5 to 12% $CO_2$ preferably 10% $CO_2$, preferably 10% $CO_2$. All passages envisaging cells or culture media handling operations are performed in sterile conditions, e.g. in a vertical laminar flow Biohazard hood (class 100).

According to a particularly preferred embodiment, the pre-amplification culture is started from a frozen MCB (Master Cell Bank) culture tube or vial, stored in liquid nitrogen and containing $1 \times 10^7$ to $2 \times 10^7$ cells/tube/ml which is thawed out in a thermostatic bath at 37° C.

The vial content is added, in a laminar flow hood, with an 8 to 10 times higher volume of cold thawing solution (complete IMDM comprising 20% FBS). The cells are centrifuged (at 1500 rpm for 10 min). Once the supernatant has been aspirated off, the cell pellet is added with 10 ml complete medium and resuspended cells are caused to pass into a T25 flask. IL-2, diluted with complete medium, is added to a final concentration of about 100 IU/ml. When the cell density obtained is such that the cells occupy the whole flask surface, as observed under an inverted microscope, the cell culture is expanded in twice the medium volume (and amplified in two T25 flasks). For this purpose, an equal volume of fresh medium is added and the culture is split into two equal flasks to restore the optimal cellular density (inoculum cellular density), which generally ranges from 0.7 to $1 \times 10^6$ cells/ml, and wherein the volume of each flask corresponds to the initial volume.

To maintain an optimal gas exchange in the culture medium, the optimal cell culture medium volume in a T25 flask is comprised from 7 to 12 ml, preferably 10 ml; of a T75 flask it is from 20 to 60 ml, preferably 40 ml; of a T175 flask it is from 40 to 200 ml. The above volumes are approximate and are referred to optimal cellular density conditions.

After thawing, the optimal cellular density is usually reached after 3 to 7 days, preferably after 5 days. After approx. 3 days, the cells are caused to pass from 2 T25 flasks into 2 T75 flasks; the cells left in the flask, if any, are harvested; IL-2 is added to the fresh medium according to the above indicated concentration.

After approx. 3 days, the cells are caused to pass from 2 T75 flasks into 2 T175 flasks. The cells left in T75 flasks, if any, are harvested with washing in complete medium to reach a final volume of 40 ml and added with IL-2 in proportion. After 2-3 days, the cells are caused to pass from 2 TI 75 flasks into 4 20 ml T175 flasks, whereto the same volume of complete medium and IL-2 in proportion are Immediately added. After 2 days, the cells are caused to pass from 4 T175 flasks into 8 T175 flasks. Each T175 flask is added with approx. 20 ml complete medium and IL-2 in proportion. After approx. 2 days, the 8 T175 flasks are added with approx. 40 ml complete medium comprising human serum in concentration ranging from 2% to 10%, preferably from 4% to 6%, more preferably of 5%, and IL-2 in proportion. After 2 days, the 8 T175 flasks are added with approx. 80 ml complete medium containing IL-2 in proportion.

The final harvest volume of T175 flask usually ranges from 140 to 180 ml. The pre-amplification phase is completed after approx. 15 days with a number of cells ranging from $0.9 \times 10^9$ to $1.1 \times 10^9$ (which value generally corresponds to 8 T175 flasks, each containing 160 ml cell suspension) in a medium containing human serum in a final concentration comprised from 2% to 5%, preferably from 3% to 4%, and optionally foetal bovine serum (FBS) in a final concentration from 0.0 to 5%, preferably from 1.5% to 3%.

The passage from the medium containing FBS to the medium containing human serum preferably occurs during the two last passages of the pre-amplification phase in flask, preferably T175, preferably by successive dilutions of the culture containing FBS with fresh medium containing human serum.

Inoculum into cell-factory is performed with a number of cells ranging from 1.5 to $2.5 \times 10^7$/chamber in a volume ranging from ⅙ to ⅒, preferably ⅛, of the cell-factory final volume capacity. For the inoculum into a 10-chamber cell-factory having a final capacity of 2 litres, the inoculum is performed with 1.5 to $2.5 \times 10^8$ in a medium volume from 200 to 330 ml, preferably 230 to 270 ml, immediately added with the same volume of fresh complete medium containing 10% max, preferably 5%, human serum and cytokins, preferably interleukins, more preferably IL-2 or IL-15, still more preferably IL-2, in a final concentration from 80 to 120 IU/ml, preferably 100 IU/ml.

Every 3-5 days, preferably every 4 days, during which time the cells generally duplicate, a volume of complete medium corresponding to that contained in the cell-factory is added to continue the cell expansion and growth up to a max final volume of 2 litres/10-chamber cell-factory and to a number of cells of 1.5 to $2.5 \times 10^9$. The amplification of TALL cells in cell-factory requires the addition of fresh medium containing human serum in an amount of 10% max, preferably from 3 to 7%, more preferably from 4 to 6%, still more preferably of 5%. Therefore, in the amplification phase in the homogeneous culture system according to the invention, preferably no or little foetal bovine serum is used. Traces of FBS, if any, which maybe present at the end of the process of the invention, are the result of successive dilutions of medium containing FBS with the medium containing human serum.

Briefly, according to a procedure general scheme, both in the pre-amplification phase in flask and in the expansion phase in the homogeneous system, the cellular density, at the inoculum is never below $0.7 \times 10^6$ cells/ml (which value corresponds to the value obtainable by splitting the cell culture into 2 or into 3 every 48-72 hrs) and is preferably $0.75 \times 10^6$/ml. Conversely, in the final growth phase, shortly before cells harvesting, it never exceeds $2 \times 10^6$ and is preferably $1.5 \times 10^6$/ml.

The volumes and the number of cells according to the process of the invention—in which the inoculum is performed into a 40-chamber cell-factory with a medium max capacity of 8 litres and capable of supplying a total amount of cells grown in a single homogeneous system of approx. $8-10 \times 10^9$, have been proportionally calculated.

According to the process of the present invention, at least one bag containing the highest therapeutic dose of TALL cells, i.e. $2.5 \times 10^9$ cells (bags containing $1 \times 10^8$ to $2.5 \times 10^9$ cells), can be produced by a homogeneous culture system. Therefore, according to a further embodiment of the invention, the process embraces also the preparation of frozen bags of TALL lymphocytes in an amount of at least $1 \times 10^9$, characterized by the fact said that TALL cells are expanded in a homogeneous culture system. The bags used have a variable volume and, therefore, contain different therapeutic doses of cells. Bags for freezing and for infusion are preferably used, more preferably Baxter Cryocyte's bags.

To prepare bags for therapeutic use, cells from the cell-factory at the harvest, are placed in a 50 ml sterile tube and irradiated, according to methods known to the art, in a beta particle accelerator (betatron). The method has been validated so as to supply the same amount of particles as that supplied by a traditional source, such as Cs137. The method using the betatron has the advantage that it is not radioactive and brings about a uniform irradiation of the solution. Once irradiated, the cells are centrifuged (at 1500 rpm for 10 min). At this point, a sample of cells is withdrawn for qualitative tests.

The irradiated cells together with the final suspension components and the sterile bags are placed in a laminar flow hood. The cells are resuspended in the freezing solution consisting of Rimso 50 (50% DMSO) (20%) and of 5% human albumin (80%) in 8 to 30 ml medium, more preferably in 10 to 25 ml complete medium containing TALL cell doses in the range of $1 \times 10^8$ to $2.5 \times 10^9$. Preferably, the cellular density in the bag ranges from $10^6$ to $10^8$ cells/ml. The irradiated cells may be stored at 4° C. for no more than 24 hrs before freezing.

The cell concentration is evaluated by count, under a microscope, in Burker's chamber, or by other methods known to those skilled in the art. Bags are filled in sterile conditions.

Once the bags have been filled, they are sealed, e.g. by hot sealing, transversally to the bag filling collet, in two, preferably three points, to create one or preferably two chambers which contain cells, and wherein such cells are called "authentic samples" for the purpose of the present invention. The cells aliquots contained in the two bag collet portions are separate but derive from the same culture batch.

According to a preferred embodiment of the invention, the volume of the cells suspension contained in the collet chambers ranges from 0.1 to 1 ml, preferably 0.3 ml, and the number of cells/chamber is sufficient for at least a series of appropriate quality and/or sterility controls. The cells of the chamber/s corresponding to the authentic samples, may be easily withdrawn without opening the whole bag.

Said chambers containing the "authentic samples", the method of sealing the bag collet in one or more points and the method of formation of the bag authentic samples are further objects of the present invention.

The bags for cryopreservation and infusion are frozen at −80° C.

It is a further object of the present invention to provide a process for the preparation of frozen bags of TALL lymphocytes in an amount of at least $1 \times 10^9$ cells, wherein said amount derives from a single homogeneous culture system.

The quality controls on cells amplified according to the process of the invention may be performed before freezing upon cells harvesting from the homogeneous culture system as well as after freezing, and are meant for checking the stability of the properties, such as the percent amounts of immunologic markers and the biological activity of the TALL cells finished product. The cells produced according to the invention are stable also after freezing.

The quality controls preferably comprise the following measurements performed according to methods known to the art:

viability, preferably determined by the Trypan Blue exclusion test; it must be 80% min;

biological activity, preferably determined by a cytotoxicity test (adenylate-kinase measurement), although alternative tests may also be used; it must be higher than a 60% lysis of target cells, K562, in a 10/1 ratio;

endotoxin levels, preferably determined by the Lymulus Amebocyte Lysate colourimetric test; they must be $\leqq 0.5$ EU/mL;

immunologic markers phenotype, preferably determined by immunofluorescence (FACS), which must give values of at least 90% for the markers known as $CD3^+$, $CD8^+$, $CD56^+$;

proliferation, preferably performed by the $^3$H-TdR incorporation test: the proliferation measured after 72 hrs at least must be higher than or equal to twice the background value.

According to the method of the present invention, the parameter measured such as the percent of immunologic markers, the biological activity, and the activity of metabolic markers, such as for example the glucose level of the culture medium, are less variable in cell grown in the homogenous system than those measured on cells grown in a heterogeneous culture system.

In fact, in the cell-factory homogeneous culture system, the percentage of immunologic markers expressed on TALL cells is at least 90%, more preferably at least 95% more preferably at least 98%, for $CD3^+$ and $CD56^+$; and at least 90%, more preferably at least 93% for $CD8^+$, whereas it is lower for cells grown in flask. The value of $CD56^+$ marker expression which results preferably at least 95% min, preferably at least 97%, is higher in the process of the invention than in cells grown in the heterogeneous flask system. Also the biological activity determined by the cytotoxicity test on target cells, which are usually preferably K562, is higher than the acceptable limit and is always higher than 70% compared to the control which consists of an appropriate number of cells where lysis has been completely induced. According to a further embodiment the invention comprises the TALL lymphocytes, preferably TALL 104, obtainable according to the process of the invention.

Also the glucose levels measured proves that the metabolic conditions of the cells are more homogeneous in cells grown in cell-factory according to the process of the invention with respect to those grown in flasks (FIG. 1): in fact, while the measurements in flask give glucose concentrations ranging from 300 to 400 mg/dl, the measurements in cell-factory give values ranging from 350 to 380 mg/dl. According to a simplified embodiment, the process of the invention comprises any TALL cell culture pre-amplification phase performed according to methods known to the art, comprising an inoculum in cell-factory of $2 \times 10^7$ cells/chamber, in an initial volume of 1/10 to 1/6 of the cell-factory final volume, and a cell-amplification phase in cell-factory, preferably in a 10-chamber cell-factory (with a final capacity of approx. 2 L), with a total inoculum of approximately $2 \times 10^8$ cells in about 250 ml.

Under the conditions adopted in the present procedure, in the large-scale expansion in cell-factory, the ratio of minimum inoculum density to the maximum recovery density at the end of the expansion cycle is optimised. In fact, according to the method of the present invention, at the end of the expansion cycle the number of cells is approx. ten times greater (from 1.5 to $2.5 \times 10^8$ cells to 1.5 to $2.5 \times 10^9$ cells), whereas the volume is only 8 times higher. The further advantages of the homogeneous culture system are: 1) elimination of the cell growth heterogeneity conditions, 2) reduced number of handling operations and, consequently, reduced possibility of contamination, 3) reduced man-hours and personnel costs.

A further advantage of the procedure according to the invention, which derives from a reduced contamination risk in respect of culture systems in multiple flasks, is the use of an antibiotic-free culture medium.

A still further advantage of the procedure according to the invention is the use of a human serum concentration preferably of 10% max. Therefore, according to the procedure of the invention, a satisfactory cell amplification is obtained with a human serum concentration preferably ranging from 4 to 6%.

Therefore, by performing the expansion phase in cell-factory, the whole procedure for the preparation of the bag for the therapeutic use of TALL is optimised and is suitable for large-scale application.

The advantages of the TALL expansion method according to the present invention may be summarized as follows: i) the quality controls are limited to a single sampling unit which corresponds to a single production unit (cell-factory); conversely, the possibility of contamination increases when the expansion Is obtained by amplification in a much greater number of single fermentation units, worked at different times and, consequently, liable to increased risks of contamination; ii) the use of a limited number of bioreactors results in ca. 30% time-saving and a 25% cost reduction.

It is to be noted that, according to the methods already known to the art for this type of cells, the amount of $2.5 \times 10^9$ cells, corresponding to approx. 0.25 $10^8$ cell bags or to 1 $2.5 \times 10^9$ cell bag was obtained with 35 T175 and with a volume of complete medium of 2.8 L. It follows that, by the method according to the present invention, the saving in raw materials (human serum, medium, cytokines) is as high as approx. 30%.

A further advantage is obtained on the number of controls conducted on the final lots, which consist of $1 \times 10^8$ cells max in the heterogeneous system known to the art and of a 10 times greater number in the lot produced by the homogeneous system described in the present invention. In practice, this means that the number of controls is 10 times lower.

EXPERIMENTAL EXAMPLES

1. Materials

Flasks: Falcon, Beckton Dikinson;

cell factory: cat. No. 164327 or 170009, Nunc A/S, Denmark; www.nuncbrand.com;

culture medium: Iscove's Modified Dulbecco Medium, Biowhittaker 12-722, supplemented with glutamine;

CM (Complete Medium) containing glutamine and serum;

foetal bovine serum: Biowhittaker, USA;

human serum, type AB, Biowhittaker;

IL-2 Proleukin 1, Chiron;

saline solution: phosphate buffered saline, Biowhittaker;

human albumin (5%), Farma Biagini;

RIMSO 50, Baxter;

bags for cryopreservation and infusion, Cryocyte Baxter.

2. Methods

All cell cultures were performed in a sterile environment, in Biohazard's hood. At every addition or withdrawal, inlet spouts were disinfected with isopropanol or with the flame.

2.1. Medium Preparation

Serum lots were uncomplemented in a thermostatic bath at 56° C. for 1 h. Uncomplemented serum bottles were kept at 4° C. and used within one month from the date of uncomplementation.

2.2. Complete Medium for the Pre-Amplification Phase

A 500 ml IMDM bottle was added with uncomplemented FBS (50 ml); the bottle was identified with the lot. The complete medium was stored at 4° C. and heated to room temperature before use. The complete medium was used within one month from the date of preparation.

2.3. Complete Medium for Scale Up in Cell-Factory

A 500 ml IMDM bottle was added with 25 ml uncomplemented human serum AB. The medium was stored at 4° C. and heated to room temperature before use. The complete medium was used within one month from the date of preparation.

2.4. IL-2 Preparation

Interleukin ($18 \times 10^6$ IU/vial) was resuspended in 20 ml PBS to obtain approx. $9 \times 10^5$ IU/ml. The resulting solution was filtered through 0.22 μm filters and the vials were dispensed in 1 ml aliquots. The aliquots were stored at −80° C.

This solution (1 ml) was diluted with complete medium, corresponding to the medium of point 2.2. for the pre-amplification phase, then with a medium corresponding to point 2.3. for the amplification phase, to obtain a $10^4$ IU/ml solution. Said solution was added to the cell suspension, by diluting same (1/100) with the culture medium.

2.5. Process Controls

Bioburden: The microbial contamination was determined on the complete medium used to grow TALL cell lines (IMDM+supplemented serum). The resulting medium was filtered through a membrane with 0.45 μm pores, the filter was removed by a sterile lancet and placed in an appropriate medium for the visualisation of the micro-organisms contamination (the medium used was Tryptic soy agar). The filter was laid on the plate. The presence of moulds was detected after incubation at 20-25° C. for 3 days at least and the presence of bacteria was detected after further incubation at 30-35° C. for at least 3 days. Plates were visually inspected to check the growth of micro-organisms (100 CFU AT maximum).

Microbiologic monitoring: The hoods used for TALL processing were controlled to check whether micro-organisms, If any, were present during the procedure. While the operator was working on the cells (pouring, bags filling), a Petri dish with TSB agar was exposed in the hood, covered upon process completion, and incubated at 20-25° C. for 3 days at least to detect the presence of moulds and at 30-35° C. for 3 days at least to detect the presence of bacteria. Micro-organisms were found during sampling in two cases of flasks handling operations, whereas no contamination was detected in the cell-factories handling operations.

Example 1

Laboratory-Scale Thawing and Amplification

A thawing solution consisting of IMDM medium supplemented with 20% FBS was prepared and kept at 4° C. before use.

An ampoule containing frozen cells was taken from the nitrogen drum, thawed appropriately, and diluted (1:10) with the thawing medium. The cells were centrifuged at a low rate for 10'. The pellet was resuspended in 10 ml complete medium, caused to pass into a T25 flask, and added with IL-2 up to a concentration of 100 IU/ml.

The cells were incubated at 37° C. for 5 days in an environment containing 10% $CO_2$.

After a 5-day incubation, the cells were split (1:2) in a fresh medium containing the same concentration of interleukin 2 and allowed to grow to confluence, which was maintained for 2 days. The cells were gently removed from the flask and caused to pass into a T75 flask containing a final medium volume of 20 ml and the same IL-2 concentration (100 IU/ml). Once confluence had been reached in approx. 2-3 days, the cells were allowed to stand for 2 further days and then amplified in a T175 flask with a final medium volume of 40 ml and IL-2 (100 IU/ml). Two days later, further 40 ml of interleukin complete medium was added; the cells were allowed to grow for 2 further days and split (1:2) into 2 other T175 flasks in a final volume of 80 ml/T175.

The cells morphology and density were examined under a microscope. Then the cells were brought to a final volume of 150 ml/flask in 5% complete medium (IMDM containing human serum AB) and added with IL-2 in proportion.

The cells were split (1:2) into the same number of T175 flasks in a final volume of 150 ml.

Example 2

TALL Cells Dynamic Growth in miniPERM Fermentor and Spinner Flask

The cells were thawed, cultured in T25 and amplified up to a number of $7 \times 10^5$ cells/ml for inoculation into 0.5 L spinner flask or in miniPERM.

Some measurements meant to set up the growth parameters were performed in flask T75: the cells were split when they reached a concentration of at least $1 \times 10^8$/ml. To maintain a high cell viability (90% min) and a higher cell splitting rate, the cells dilution was never below $7 \times 10^5$ cells/ml and the cells growth never exceeded $2 \times 10^6$/ml. At the max cell concentration, the glucose level was approx. 320-380 mg/ml. In T175, in 80 ml final volume, a concentration of $1.25 \times 10^6$ cells/ml, corresponding to a total of approx. $100 \times 10^6$ cells/flask, was obtained.

It was assessed that, for a higher viability during freezing/thawing, the minimum number of cells/vial had to be higher than $1.2 \times 10^7$. It was also observed that cells frozen in the logarithmic growth phase, on their turn reached the logarithmic growth phase after thawing, within 9-10 days, whereas the cells frozen in other growth cycle phases exhibited a higher time lag (10-12 days).

Spinner flask. The 0.5 L spinner flask had 300 ml working volume. Inoculation was performed with $1.5 \times 10^7$ cells; spinning was set at 3 rpm; cell viability was measured 48 hrs later and was found to equal 50%. 120 hrs later, all cells were dead.

Furthermore, 3 amplification tests were performed in MiniPERM (a bioreactor with a high surface in respect of its volume, ideal for the expansion of cells in suspension, such as hybridoma cells) using 10% $CO_2$ and adopting the following specific conditions:

inoculation with $7 \times 10^7$ cells in 30 ml at 10 rpm. The cell viability started decreasing already after 48 hrs and all cells were dead after 4 days. In the second test, the spinning rate was decreased to 5 rpm. On the third day of growth, the cell viability was 52%; on the 6th day all cells were dead. In the third test, the inoculation was decreased to $3 \times 10^7$ cells and the spinning rate was decreased to 4 rpm. Although all cells had died off within the 5th culture day, on the 2nd day the cell viability was still fairly high (80%); this suggested how important spinning is to cells survival. Both preliminary fermentation tests had demonstrated that T-ALL cells could not grow in the traditional large-scale growth conditions commonly used for cells in suspension or anchorage-independent.

Example 3

Large-Scale TALL Amplification in Cell-Factory

A cell suspension (250 ml), obtained from the growth in T175 as per Example 1 and containing approx. $0.8 \times 10^6$ cells/ml, were inoculated into a 10-chamber cell-factory; the same amount of complete medium was added. Four days later, complete medium was added (500 ml×3 times) up to a total volume of 2 L.

The cell-factory was emptied into 250 ml sterile vials—which were centrifuged—and washed with sterile PBS; the cells were recovered in vials and centrifuged again. Eight days after inoculation, the cells recovered from a cell-factory were approx. $2.35 \times 10^9$.

In a typical production cycle in a 10-chamber cell-factory, 72 inoculations and amplifications from a single MCB (Master Cell Bank) frozen vial were performed. Total duration: 120 days, total cell culture: 144 litres. The cells obtained were approx. $1.44 \times 10^{11}$.

Table 1 shows the data obtained from a fermentation in a 10-chamber cell-factory and in a 40-chamber cell-factory, respectively.

TABLE 1

Yields obtained in a 10-chamber cell-factory and in a 40-chamber cell-factory

|  | Cell factory 10 (2 liters) | Cell factory 40 (8 liters) |
|---|---|---|
| No. inoculations | 72 | 31 |
| Days | 120 | 120 |
| Volumes (liters) | 144 | 248 |
| No. of cells | $1.44 \times 10^{11}$ | $2.48 \times 10^{11}$ |

The cell-factory cells content was combined in a 50 ml sterile vial and irradiated, as known, in a beta particle accelerator (betatron). The method had been validated so as to supply the same amount of particles as that supplied by a traditional source, such as Cs137. The method using the betatron has the advantage that it is not radioactive and brings about a uniform irradiation of the solution.

Bags preparation. Once irradiated, the cells were centrifuged (at 1500 rpm for 10 min). A sample of cells was withdrawn for qualitative tests and stored at 4° C. before freezing.

The irradiated cells, together with the final suspension components and the sterile bags, were placed in a laminar flow hood. The cells were resuspended in the freezing solution, which consisted of Rimso 50 (50% DMSO) (20%) and 5% human albumin (80%), depending on the amount of cells necessary for a therapeutic dose. The cells were counted under a microscope in Burker's chamber and the bags were filled with the appropriate volume in sterile conditions. Once the bags had been filled, the filling collet was sealed in three points; each bag thus formed an authentic sample.

The cell-factory>irradiation>bags cycle was repeated a number of times sufficient to obtain the number of cells required by the lot.

Sterility Controls

Bioburden sterility controls, microbiological monitoring and mycoplasma monitoring were continuously performed on media and hoods.

Example 4

Controls on the Finished Product and Comparison Between Laboratory-Scale and Large-Scale Growth Measurement of glucose levels: the glucose levels were measured on a sample of 15 flasks (out of the 35 flasks corresponding to the amount of cells in a cell-factory) upon cells harvesting for bag preparation. As shown in FIG. 1, the glucose concentration and the number of cells are highly variable; conversely, in a 10-chamber cell-factory, upon harvesting (after 6-10 days) glucose shows one value (approx. 380 mg/dl) and the cells have one density ($2 \times 10^9$/ml). The different glucose levels and the different cell concentrations found in flask are indicative of non-homogeneous metabolic conditions: in fact, high glucose levels in the medium correlate with a low metabolic activity of the cell culture, whereas low glucose levels correspond to a high metabolic activity of the cell culture.

Final Product Quality Control

The controls listed in Table 2 were performed on irradiated cells. The acceptability limits of the values are reported in the column on the right.

TABLE 2

| Assay | Method | Limits |
|---|---|---|
| Viability | Trypan Blue exclusion test | >80% |
| Biological activity | Cytotoxicity test | >60% lysis of target cells K562 in a 10/1 ratio |
| Endotoxins | Lymulus Amebocyte Lysate colourimetric test | $\leq 0.5$ EU/mL |
| Phenotype | Immunofluorescence (FACS) | $\geq 90\%$ CD3$^+$, CD8$^+$, CD56$^+$ |
| Proliferation | $^3$H-TdR incorporation | $\leq$twice the background after 4-day incubation |

Viability Test

The determination was performed by diluting 100 µl cell suspension before bagging with a 100 µl Trypan Blue solution. After an appropriate dilution, a control was performed under a microscope by counting the dyed cells in Burker's chamber.

Biological Activity

The determination of cytotoxicity was performed on the cell suspension, before bagging, with a kit Toxilight™ (BioWhittaker LT07-217). The method is based on the measurement of adenylate-kinase by bioluminescence. Adenylate-kinase is released from the cells when they lose the membrane integrity and converts the substrate ADP into ATP in the presence of Mg$^{++}$, thus allowing its measurement. The determination was performed by plating $10^5$ target cells, K562, onto a many-well microplate; cells prepared according to the method were added, in amounts of $10^6$, $5 \times 10^5$ and $2.5 \times 10^5$, to obtain T/K (or effector/target) ratios equal to 10.5 and 2.5, respectively.

Once the target cells were incubated overnight, the % lysis of K562 produced by cells prepared according to the method of the present invention, was always $\geq 70\%$ of the maximum consisting of a sample of $10^5$ K562 cells lysed by ultrasounds.

Endotoxins

The endotoxins content was determined on a sample with collets prepared as mentioned above, at neutral pH, using a kit for the chromogenic LAL test and applying the method described in *European Pharmacopoeia*, 4$^{th}$ Edition, 2002, pp. 140-145.

Phenotype

The phenotype determination by measurement of the cell markers before bagging was performed by immunofluorescence (FACS) with appropriate immunologic markers (CD3$^+$, CD8$^+$, CD56$^+$) available from Molmed's Quality Control Labs.

TABLE 3

Phenotypic markers of T-ALL cells grown in flask and in cell-factory upon cells harvesting

| Amplification | | CD3 | CD8 | CD56 | Cytotox.act. | $^3$H thymidine |
|---|---|---|---|---|---|---|
| Flask | | >90% | >90% | >90% | — | ≤twice the background after 4-day incubation |
| Cell-factory avg | | >98% | >93% | ≧97% | ≧70% | ≤twice the background after 4-day incubation |
| Lot 1 | pre | 99% | 90 | 98 | | |
| | post | 99% | — | 99 | | |
| Lot 2 | pre | 99 | 98 | 99 | | |
| | post | 99 | 93 | 99 | | |
| Lot 3 | pre | 99 | 97 | 92 | | |
| | post | 99 | 94 | 95 | | | pre: pre-irradiation;
post: post-irradiation;
avg: average.

Proliferation Test

The absence of T-ALL proliferation was determined by measuring the incorporation of tritiated thymidine. A sample of the cell suspension taken before bagging was incubated in microplates at different concentrations in complete medium (IMDM+serum+IL-2) for 4 days. $^3$H-TdR (2 μCi/ml, 50 μl/well) was added. After 3-hr incubation at 37° C., the radioactivity was measured. The cpm referred to TALL cells must be ≤twice the background.

Table 3 shows the data concerning the proliferation of a cell batch grown in flask and In cell factory, respectively.

Table 4 reports the data concerning the measurement (on different preparations) of the presence of immunologic markers, of cell viability, sterility and contamination by mycoplasma, if any, after culture irradiation.

TABLE 4

Measurement of markers on TALL cells after irradiation

| No. of samples | cells | Cytofluorimetry | | | $^3$H Thymidine incorp. | | Sterility | myco |
|---|---|---|---|---|---|---|---|---|
| | | CD3 | CD8 | CD56 | sample | background | | |
| 2 | 2.5 × 10$^9$ | 99.59 | 94.8 | 92.51 | 24 | 27 | OK | negative |
| 6 | 2.5 × 10$^9$ | 99.8 | 91.34 | 97.17 | 33 | 27 | OK | negative |
| 8 | 2.5 × 10$^9$ | 99.88 | 93 | 97.84 | 37 | 26 | OK | negative |
| 18 | 1 × 10$^8$ | 99.59 | 94.8 | 92.51 | 24 | 27 | OK | negative |

| No. of samples | cells | Cytofluorimetry | | | Thymidine incorp. | | Sterility | myco |
|---|---|---|---|---|---|---|---|---|
| | | CD3 | CD8 | CD56 | sample | background | | |
| 1 | 2.5 × 10$^9$ | 99.54 | 94.63 | 95.83 | 23 | 24 | OK | negative |
| 1 | 2.5 × 10$^9$ | 99.44 | 96.24 | 98.51 | 37 | 26 | OK | negative |
| 8 | 1 × 10$^8$ | 99.54 | 93.36 | 99.79 | 34 | 25 | OK | negative |
| 7 | 0.5 × 10$^9$ | 99.8 | 92.3 | 97.05 | 82 | 60 | OK | negative |
| 11 | 0.5 × 10$^9$ | 99.54 | 93.36 | 99.79 | 29 | 29 | OK | negative |

What is claimed is:

1. A process for amplifying TALL-104 lymphocytes in a homogeneous culture system within a multi-chamber stack comprising:
   adding into the multi-chamber stack an inoculum of at least 0.7×10$^6$ TALL-104 cells/ml in an initial volume from 1/10 to 1/6 of the multi-chamber stack volume capacity and the same volume of fresh antibiotic-free complete medium, wherein said medium comprises interleukin-2 (IL-2);
   amplifying the cell number by adding a volume of said complete medium corresponding to the volume contained in the multi-chamber stack every 3-5 days; and
   harvesting at least 1×10$^9$ TALL-104 cells grown in homogeneous conditions.

2. The process as claimed in claim 1, wherein said process for amplifying TALL-104 lymphocytes is preceded by a process of pre-expansion in a flask until obtaining a number of cells in an amount from 3×10$^8$ to 4×10$^8$.

3. The process as claimed in claim 1, wherein the cellular density of the inoculum is 0.75×10$^6$ cells/ml and, at the harvesting step, the density is lower than 2×10$^6$ cells/ml.

4. The process as claimed in claim 1, wherein the multi-chamber stack is a 10-chamber unit.

5. The process as claimed in claim 1, wherein said TALL-104 lymphocytes are genetically modified.

6. The process as claimed in claim 1, wherein the complete culture medium in the multi-chamber stack amplification phase also comprises a maximum of 10% human serum and IL-2 in a concentration from 80 to 120 IU/ml.

7. The process as claimed in claim 6 wherein said complete culture medium comprises 4-6% human serum.

8. A process according to claim 6, wherein said TALL-104 lymphocytes are genetically modified.

9. A process for the preparation of frozen bags of TALL-104 lymphocytes in an amount of at least 1×10$^9$ cells comprising:
   a. recovering at least 1×10$^9$ TALL-104 cells grown in a homogeneous culture system in a multi-chamber stack according to claim 1;

b. centrifuging the TALL-104 cells;

c. collecting the TALL-104 cells into bags; and d. freezing the bags.

10. The process as claimed in claim 9, wherein the bags are sealed transversally to a bag filling collet at least in two points to create at least a sampling chamber containing a cell culture volume ranging from 0.1 to 1 ml, physically separated from the culture contained in the bag to perform quality controls.

11. A process for the preparation of a therapeutic dose of at least $1\times10^9$ TALL-104 lymphocytes in a homogeneous culture system comprising using the process according to claim 1.

12. The process of claim 11, wherein the complete culture medium in the multi-chamber stack amplification phase also comprises a maximum of 10% human serum and IL-2 in a concentration from 80 to 120 IU/ml.

* * * * *